United States Patent

Shluzas et al.

[11] Patent Number: 6,051,006
[45] Date of Patent: Apr. 18, 2000

[54] SUTURE-PASSING FORCEPS

[75] Inventors: Alan E. Shluzas, Millis; George Sikora, Mansfield, both of Mass.

[73] Assignee: Smith & Nephew, Inc., Memphis, Tenn.

[21] Appl. No.: 09/290,203

[22] Filed: Apr. 12, 1999

[51] Int. Cl.$^7$ ................................................ A61B 17/04
[52] U.S. Cl. ........................................ 606/148; 606/144
[58] Field of Search ................................. 606/148, 144, 606/145, 146, 147, 139, 222–224, 205–209; 128/898

[56] References Cited

U.S. PATENT DOCUMENTS

| | | |
|---|---|---|
| 919,138 | 4/1909 | Drake et al. . |
| 1,037,864 | 9/1912 | Carlson et al. . |
| 1,635,066 | 7/1927 | Wells . |
| 1,815,725 | 7/1931 | Pilling et al. . |
| 2,610,631 | 9/1952 | Calicchio . |
| 2,880,728 | 4/1959 | Rights . |
| 3,013,559 | 12/1961 | Thomas . |
| 3,349,772 | 10/1967 | Rygg . |
| 3,470,875 | 10/1969 | Johnson et al. . |
| 3,638,653 | 2/1972 | Berry . |
| 3,752,516 | 8/1973 | Mumma . |
| 3,840,017 | 10/1974 | Violante . |
| 3,842,840 | 10/1974 | Schweizer . |
| 3,871,379 | 3/1975 | Clarke . |
| 3,901,244 | 8/1975 | Schweizer . |
| 3,946,740 | 3/1976 | Bassett . |
| 4,161,951 | 7/1979 | Scanlan, Jr. . |
| 4,164,225 | 8/1979 | Johnson et al. . |
| 4,224,947 | 9/1980 | Fukuda . |
| 4,312,337 | 1/1982 | Donohue . |
| 4,493,323 | 1/1985 | Albright et al. . |
| 4,596,249 | 6/1986 | Freda et al. . |
| 4,602,635 | 7/1986 | Mulhollan et al. . |
| 4,621,640 | 11/1986 | Mulhollan et al. . |
| 4,641,652 | 2/1987 | Hutterer et al. . |
| 4,643,178 | 2/1987 | Nastari et al. . |
| 4,779,616 | 10/1988 | Johnson . |
| 4,781,190 | 11/1988 | Lee . |
| 4,890,615 | 1/1990 | Caspari et al. . |
| 4,923,461 | 5/1990 | Caspari et al. ........................ 606/146 |
| 4,957,498 | 9/1990 | Caspari et al. ........................ 606/146 |
| 4,961,741 | 10/1990 | Hayhurst ............................... 606/139 |
| 5,084,058 | 1/1992 | Li ........................................... 606/148 |

(List continued on next page.)

FOREIGN PATENT DOCUMENTS

| | | |
|---|---|---|
| 0 788 004 A1 | 6/1997 | European Pat. Off. . |
| WO 95/02363 | 1/1995 | WIPO . |
| WO 96/39946 | 12/1996 | WIPO . |
| WO 96/39948 | 12/1996 | WIPO . |

OTHER PUBLICATIONS

Smith & Nephew Brochure: Acufex Suture Punch, 1997.
Smith & Nephew Dyonics Brochure: Proline Reusable Endoscopic Hand Instruments, 1994.
Auto Suture Company Brochure: Endoscopic Sututing Made Easy, 1994.

Primary Examiner—Gary Jackson
Assistant Examiner—Vikki Trinh
Attorney, Agent, or Firm—Fish & Richardson P.C.

[57] ABSTRACT

A surgical instrument (e.g., suture-passing forceps) has a first jaw with a mount which supports a needled suture and a second jaw having a passage, which when aligned with the mount, is positioned to receive the needled suture. The second jaw is positioned relative to the mount in a manner which allows delivery of the instrument to a surgical site in a low profile, delivery position (e.g., with the jaws spaced relatively closely). The surgical instrument includes an elongated shaft having a distal region for supporting the jaws. The second jaw is pivotable, with respect to the mount, between the delivery position in which the second jaw is spaced relatively closely to the mount with the passage misaligned with the mount and an open, misaligned position, the second jaw being axially translatable relative to the mount to an open, aligned position in which the passage is aligned with the mount.

22 Claims, 7 Drawing Sheets

U.S. PATENT DOCUMENTS

| | | | |
|---|---|---|---|
| 5,087,263 | 2/1992 | Li | 606/148 |
| 5,100,415 | 3/1992 | Hayhurst | 606/139 |
| 5,100,418 | 3/1992 | Yoon et al. | 606/139 |
| 5,100,421 | 3/1992 | Christoudias | 606/147 |
| 5,133,723 | 7/1992 | Li et al. | 606/148 |
| 5,149,329 | 9/1992 | Richardson | 604/272 |
| 5,163,946 | 11/1992 | Li | 606/148 |
| 5,176,691 | 1/1993 | Pierce | 606/148 |
| 5,181,919 | 1/1993 | Bergman et al. | 606/144 |
| 5,192,287 | 3/1993 | Fournier et al. | 606/139 |
| 5,201,744 | 4/1993 | Jones | 606/148 |
| 5,217,471 | 6/1993 | Burkhart | 606/148 |
| 5,222,508 | 6/1993 | Contarini | 128/898 |
| 5,224,955 | 7/1993 | West . | |
| 5,234,443 | 8/1993 | Phan et al. | 606/148 |
| 5,234,444 | 8/1993 | Christoudias | 606/148 |
| 5,250,054 | 10/1993 | Li | 606/148 |
| 5,250,055 | 10/1993 | Moore et al. | 606/148 |
| 5,257,637 | 11/1993 | El Gazayerli | 128/898 |
| 5,259,846 | 11/1993 | Granger et al. . | |
| 5,261,917 | 11/1993 | Hasson et al. | 606/139 |
| 5,269,783 | 12/1993 | Sander . | |
| 5,269,791 | 12/1993 | Mayzels et al. | 606/148 |
| 5,281,234 | 1/1994 | Wilk et al. | 606/139 |
| 5,318,577 | 6/1994 | Li . | |
| 5,382,257 | 1/1995 | Lewis et al. . | |
| 5,387,221 | 2/1995 | Bisgaard . | |
| 5,389,103 | 2/1995 | Melzer et al. . | |
| 5,397,325 | 3/1995 | Della Badia et al. . | |
| 5,417,712 | 5/1995 | Whittaker et al. . | |
| 5,454,823 | 10/1995 | Richardson et al. . | |
| 5,578,044 | 11/1996 | Gordon . | |
| 5,730,747 | 3/1998 | Ek et al. . | |
| 5,814,054 | 9/1998 | Kortenbach et al. | 606/139 |

SUTURE-PASSING FORCEPS

BACKGROUND OF THE INVENTION

The invention relates generally to suturing instruments for passing needled sutures through body tissue.

An increasing number of surgical techniques are now performed endoscopically to reduce trauma associated with large incisions generally required in open surgery. These techniques involve extracorporeal manipulation of a surgical instrument, while viewing the surgical site with an endoscope, with both the instrument and endoscope passed through small incisions or portals of the body. The surgical instrument is often placed through an appropriately sized cannula which extends from the portal to the surgical site to facilitate maneuvering of the surgical instrument.

Arthroscopic surgery is a type of endoscopic procedure performed at the joint of the body, for example, to repair the meniscus of the knee or the rotator cuff and Bankart tendon in the shoulder. In such surgeries, suture is used to stitch and reattach torn cartilage, tendons or ligaments to tissue or bone.

One approach for arthroscopically stitching a needled suture uses a suturing forceps of the type described in U.S. Pat. No. 5,730,747 entitled "Suture Passing Forceps," which is incorporated herein by reference. The suture-passing forceps includes upper and lower jaws with a needled suture positioned within the lower jaw during delivery to a surgical site. In its open suturing position, the damaged tissue to be stitched is placed between the upper and lower jaws and hooked on a pointed tip of a needle. The jaws are then closed by pivotal actuation to pass the needled suture from the lower jaw to the upper jaw, thereby punching the needle through the damaged tissue being sutured. The suturing process can be repeated by reinserting the needled suture into the lower jaw, where it is ready to be passed again through the tissue. A suture-passing forceps of this type offers one-step suture passing, one-handed suturing action, passive capturing of the needle within the jaws of the forceps, and complete removal of the needled suture from the suturing assembly after passing the needle and suture through the tissue.

SUMMARY OF THE INVENTION

The invention features a surgical instrument (e.g., suture-passing forceps) having a first (e.g., lower) jaw with a mount which supports a needled suture and a second (e.g., upper) jaw having a passage, which when aligned with the mount, is positioned to receive the needled suture. The second jaw is positioned relative to the mount in a manner which allows delivery of the instrument to a surgical site in a low profile, delivery position (e.g., with the jaws spaced relatively closely) in which the passage of the second jaw is misaligned with the mount.

In a general aspect of the invention, the surgical instrument includes an elongated shaft having the first and second jaws mounted at a distal region of the shaft, the second jaw is pivotable, with respect to the first jaw, between the delivery position in which the second jaw is spaced relatively closely to the mount with the passage misaligned with the mount and an open, misaligned position, the second jaw being axially translatable relative to the mount to an open, aligned position in which the passage is aligned with the mount.

Thus, the jaw is both pivotable and translatable with respect to the mount, so that the passage of the second jaw has a "misaligned" (i.e., the passage is not in position to receive the needle when the jaw is pivoted) low profile position during delivery, for example, through a narrow cannula extending to a surgical site. This low profile arrangement is achieved without manipulating the needle within its mount, an approach used in other conventional suturing assemblies. Once at the surgical site, the second jaw can be actuated to pivot away from the mount into the open, misaligned position. The second jaw can be further actuated to axially translate the jaw to an open, aligned position in which the passage is aligned with the mount.

A further advantage of misaligning the second jaw with respect to the mount is that the needle supported within the mount cannot be prematurely captured by the second jaw during delivery and manipulation of the instrument when the jaw can collide with anatomical objects (e.g., bones, vessels, muscles or tendons). Thus, the surgical instrument eliminates the need for a handle locking mechanism typically required with conventional instruments for preventing premature capturing of the needle by the second jaw during delivery.

Embodiments of this aspect of the invention may include one or more of the following features.

The second jaw is pivotable with respect to the mount between the delivery position and the open, misaligned position along a first arcuate path. The second jaw is translatable with respect to the mount along a linear path to align the passage with the mount. The second jaw is also pivotable from the open, aligned position to a closed position along a second arcuate path to receive the needle from the mount.

The second jaw includes a first pivot slot and the first jaw includes a first pivot pin movably retained within the first pivot slot. The first pivot pin defines a center of rotation for the first arcuate path. The second jaw also includes a second pivot slot and the first jaw also includes a second pivot pin movably retained within the second pivot slot. The second pivot pin defines a center of rotation for the second arcuate path. Thus, the pin and slot configuration define the first and second arcuate paths along which the second jaw pivots relative to the mount of the first jaw. For example, the first and second pivot slots each include arcuately-shaped sections extending to linear sections. As the second jaw pivots along the first arcuate path, the first pivot pin is positioned within the linear section of the first pivot slot and the second pivot pin is positioned within the arcuately-shaped section of the second pivot slot. Similarly, as the second jaw pivots along the second arcuate path, the second pivot pin is positioned within the linear section of the second pivot slot and the first pivot pin is positioned within the arcuately-shaped section of the first pivot slot.

As the second jaw translates along the linear path, the first and second pivot pins are positioned within the linear sections of the first and second pivot slots, respectively. The linear section of the first pivot slot is substantially parallel to the linear section of the second pivot slot and, when the second jaw translates along the linear path, the linear sections of the first and second pivot slots are substantially parallel to a longitudinal axis of the elongated shaft.

The passage of the second jaw is positioned proximally of the mount in the delivery position. The surgical instrument further includes an actuator having a distal end coupled to the second jaw and a handle, disposed at a proximal end of the shaft, and coupled to a proximal end of the actuator. The handle is actuatable from a fully open position to a fully closed position to apply an axial force to the actuator, thereby moving the second jaw from the delivery position; to the open, misaligned position; through the open, aligned position; and to the closed position. The surgical instrument includes a needle tip protector axially offset (e.g., proximally or distally) from the passage of the second jaw. The first jaw is stationary relative to the elongated shaft.

In another aspect of the invention, a method of delivering a suture needle to a surgical site using a surgical instrument of the type described above is provided. The method includes positioning the needle in the mount and moving the second jaw relative to the mount to position the surgical instrument in a delivery position in which the second jaw is spaced relatively close to the mount and the passage of the second jaw is misaligned with the mount. The surgical instrument is then delivered to the surgical site (e.g., through a cannula which extends from a portal to the surgical site). The second jaw is actuated relative to the mount to pivot the second jaw from the delivery position into an open, misaligned position in which the second jaw is spaced further from the mount and then further actuated to translate the second jaw relative to the mount into an open, aligned position, thereby aligning the passage with the mount.

Embodiments of this aspect of the invention may include one or more of the following steps.

The second jaw is pivoted along a first arcuate path and translated along a linear path. Once in the open, aligned position, the second jaw is actuated to pivot the surgical instrument to a closed position by punching the needle through tissue to be sutured and capturing the needle by the passage of the second jaw. After actuating the surgical instrument from the open suturing position to the closed position, the surgical instrument is withdrawn from the surgical site. The needle is then removed from the passage of the second jaw, and the needle may be repositioned in the mount of the first jaw for further suturing. The method further includes passing the surgical instrument in the delivery position through a cannula which extends from a portal to the surgical site.

The method further includes protecting a pointed tip of the needle by positioning a pointed tip of the needle within a needle tip protector formed at a distal end of the second jaw in the delivery position.

Other features and advantages will become apparent from the following description, and from the claims.

DETAILED DESCRIPTION

Figure 1:
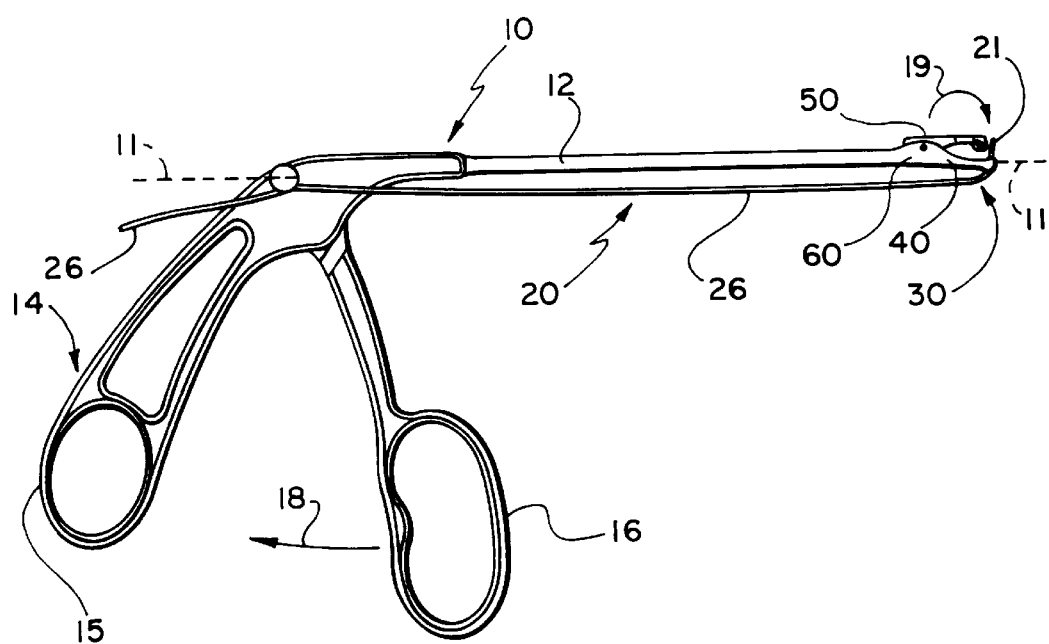
FIG. 1 shows a surgical forceps with a needled suture positioned within a mount such as a lower jaw of the forceps and an upper jaw in a delivery position.

Referring to FIG. 1, a suture-passing forceps 10 includes a suturing assembly 30 for passing a needled suture 20 through tissue requiring repair. Suturing assembly 30 has an upper jaw 50 which is movable relative to a stationary lower jaw 19 having a mount 40, between a low-profile, misaligned delivery position; an open, misaligned position; an open aligned position; and a closed position. Suturing assembly 30 is advantageously configured to have a lower profile in the delivery position than in the open suturing position, allowing the suturing assembly to be delivered through a relatively small diameter insertion devices (e.g., catheters).

In particular, in the delivery position, upper jaw 50 is spaced relatively close to, but axially misaligned with mount 40. In the axially misaligned position, pivoting upper jaw 50 relative to mount 40 by itself does not position the upper jaw so as to be able to capture needle suture 20 were the upper jaw to be pivoted closed. Instead, further movement of the upper jaw 50 is required to position the upper jaw in the aligned position. Specifically, upper jaw 50 must be axially translated into an aligned position so that the upper jaw captures needled suture 20 when the upper jaw is pivoted closed. Accordingly, and as will be described in greater detail below, upper jaw 50 is coupled to lower jaw 19 by a pivot mechanism 60 which allows the upper jaw to first pivot from the delivery position to a misaligned open position and then translate axially to an open, aligned position in which the upper jaw is aligned with the mount. In this open, aligned position, upper jaw 50 can then pivot toward mount 40 so that needled suture 20 is passed from the lower jaw to the upper jaw. Reversing this sequence causes upper jaw 50 to pivot away from mount 40, translate proximally, and pivot toward mount 40 to its original, misaligned, and lower profile delivery position.

Pivot mechanism 60, for coupling upper jaw 50 to mount 40, is connected to an actuator 17 (FIG. 2), which extends through a support shaft 12 and, in turn, is connected to an actuating handle 14. Handle 14 includes a stationary thumb section 15 and a movable finger section 16 which, upon actuation by the user, pushes actuator 17 distally along a longitudinal axis 11 of support shaft 12 to cause upper jaw 50 to both pivot and translate relative to lower jaw 40 in the manner described above.

Figure 2:
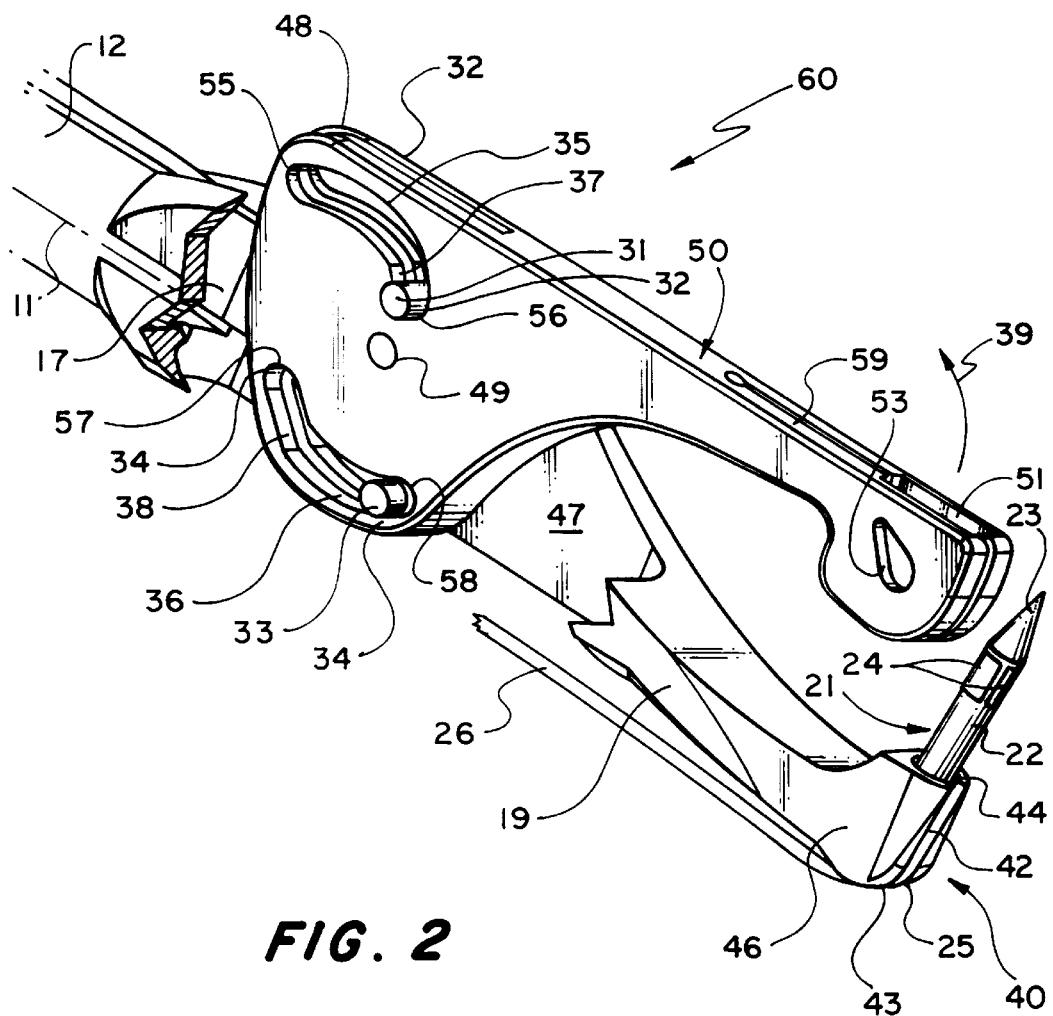
FIG. 2 is an enlarged, partially cut-away view of the distal end of the surgical instrument of FIG. 1 with the upper jaw in the delivery position.

Referring to FIG. 2, mount 40 includes a channel 47 at its proximal end which is sized to receive and movably retain a proximal end of upper jaw 50. Mount 40 serves as a needle holding region for removably holding a needle 21 of needled suture 20 attached to a suture thread 26 by, for example, crimping or clamping. The length of needle 21 is typically less than about 0.5 inches and preferably about 0.3 inches. Suture thread 26 may be, for example, #1 or #2 size sutures, monofilament or braided. Needle 21 includes a substantially straight, tubular shaped body 22 and a pointed tip 23 to facilitate passage through tissue. Needle 21 also includes flats 24 formed around the periphery of needle 21 and between pointed tip 23 and a base portion 25 of the needle.

The needle holding region of mount 40 is defined by a passage 42 which extends through the mount from a lower opening 43 to an upper opening 44 of the mount. Lower opening 43 has a diameter only slightly larger than the diameter of body 22 of needle 21. Thus, in the delivery and open positions, body 22 of needle 21 is held in place by a friction fit within lower opening 43. The needle holding region of mount 40 holds needle 21 in a slanted position relative to axis 11. That is, pointed tip 23 may be slanted proximally or distally, for example, at an angle between 60° and 120° relative to the axis of support shaft 12. Because pointed tip 23 is slanted, the possibility of needle 21 snagging tissue during delivery and prior to suturing is minimized. The needle holding region disperses mechanical stresses imparted to needle 21 to other parts of mount 40, thereby minimizing the possibility of needle 21 breaking during puncturing operations. Outer surface 46 of mount 40 is also formed without sharp corners which might cut or fray suture thread 26. In other embodiments, needle holding region 41 may also be arranged to hold needle 21 at an angle substantially perpendicular to axis 11 of support shaft 12.

Upper jaw 50 also includes, at its distal end, a needle receiving passage 51 sized to receive and capture needle 21 when jaws 19, 50 are closed after the needle passes through the tissue. Needle receiving passage 51 is defined by a slotted opening extending through upper jaw 50. A middle portion of needle receiving passage 51 is shaped and sized in a detent-like arrangement to engage flats 24 of needle 21. This detent-like arrangement in combination with the spring constant associated with the material and structure of upper jaw 50 define the spring force with which needle 21 is held within needle receiving passage 51 when, in the closing operation, upper jaw 50 receives needled suture 20. Specifically, the detent in upper jaw 50 and flats 24 provide a holding force greater than the frictional holding force of lower jaw 40 on needle 21 in lower opening 43. This difference in holding force enables needle 21 to be passed from lower jaw 40 to upper jaw 50. Upper jaw 50 also includes an opening 53 through which needle 21 can be seen, enabling the user to confirm that the needle has been properly captured by upper jaw 50. Further details relating to needle holding regions 41 and needle receiving passage 51 are described in U.S. Pat. No. 5,730,747.

Pivot mechanism 60 includes a slot and pin arrangement for allowing upper jaw 50 to pivot to the open, misaligned position and then translate axially to the open, aligned position, thereby aligning the upper jaw with mount 40. Specifically, mount 40 includes an upper pivot pin 31 and a lower pivot pin 33, each of which is press-fit into the mount and extends across channel 47 of the mount. Upper jaw 50 includes an upper pivot slot 32 and a lower pivot slot 34, each of which receives a respective one of upper and lower pivot pins 31, 33. Actuator 17 is coupled to pivot mechanism 60 by inserting a distal end of the actuator into a slot 48 formed within upper jaw 50. Actuator 17 is then secured to upper jaw 50 with an actuator pin 49 which extends through a hole 45 of the upper jaw located between upper and lower pivot slots 32, 34.

Figure 3:
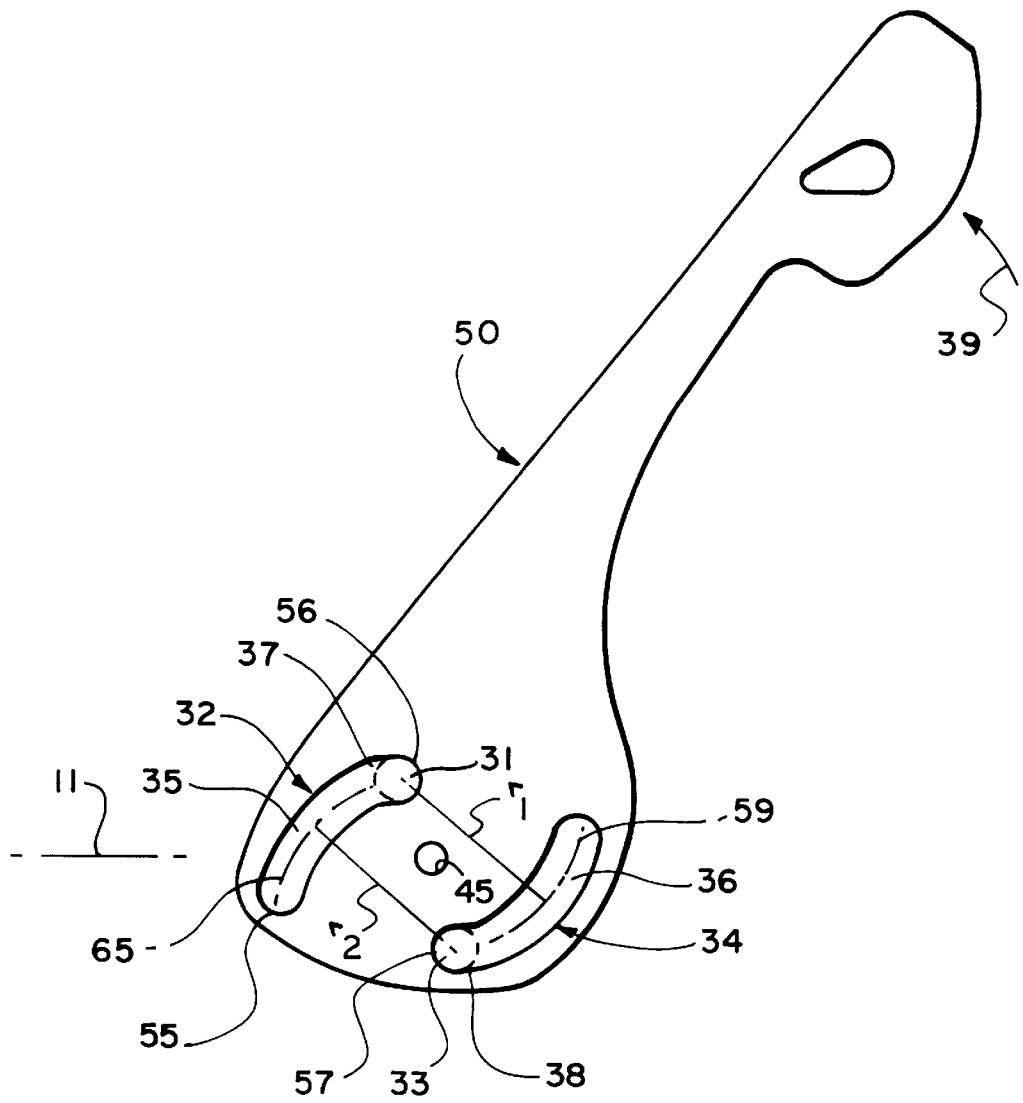
FIG. 3 is a diagrammatic side view of the upper jaw.

Referring to FIG. 3, upper pivot slot 32 has an arcuately-shaped section 35 extending distally from a proximal end 55 of the slot to a linear distal section 37. Linear section 37 in turn, extends to a distal end 56 of slot 32. Similarly, lower pivot slot 34 has an arcuately-shaped section 36 extending proximally from a proximal end 57 of the slot to a linear proximal section 38 which extends to a proximal end 58 of the slot. Linear sections 37, 38 are parallel to each other and, as shown in FIG. 3, when upper jaw 50 is in open, aligned position, the linear sections are parallel to axis 11 of support shaft 12.

In general, pivot pins 31, 33 and slots 32, 34 define two different centers of rotation and two different arcuate paths 59, 65 about which each of the pins rotate within respective ones of the slots. Arcuate path 59 is defined by arcuate section 36 of lower pivot slot 34 and has a radius ($r_1$) centered about a center of rotation defined by pivot pin 31 when pivot pin 31 is positioned within distal end 56 of upper slot 32. Arcuate path 59 corresponds to the pivoting of upper jaw 50 from the low profile, delivery position to the open, misaligned suturing position.

Arcuate path 65 is defined by arcuate section 35 of upper pivot slot 32 and has a radius ($r_2$), equal to $r_1$, centered about a center of rotation defined by pivot pin 33 positioned at proximal end 57 within linear section 38 of lower slot 34. Arcuate path 65 corresponds to the pivoting of upper jaw 50 from the open, aligned position to the closed position.

Linear translation of upper jaw 50 for aligning needle receiving passage 51 with needle 21 occurs along linear sections 37, 38 of upper and lower slots 32, 34, respectively. As shown in FIG. 3, linear translation occurs when both pivot pins 31, 33 are positioned within the linear sections, each of which is substantially parallel with axis 11 of support 12. Upper jaw 50 translates with respect to mount 40 a distance equal to the length of linear sections 37, 38.

Operation of pivot mechanism 60 will now be described in conjunction with FIGS. 2 and 4–6.

Referring again to FIG. 2, suturing assembly 30 is shown in the low profile delivery position with upper jaw 50 spaced relatively close to, but misaligned with mount 40. In particular, upper jaw 50 is axially offset proximally relative to mount 40 with needle receiving passage 51 in a position where it can not capture needle 21. In this low profile delivery position, pivot pin 31 is located at within distal end 56 of upper slot 32 and serves as the center of rotation for movement of pivot pin 33 along arcuate section 36 of lower slot 34.

In response to the user squeezing finger section 16 of handle 14, an axially (distally) directed force applied by actuator 17 causes upper jaw 50 to pivot about pivot pin 31 along arcuate path 59 of lower slot 34. Upper jaw 50, in turn, pivots away from mount 40 in the direction of arrow 39 until pivot pin 33 reaches linear section 38 of lower slot 34. Throughout this rotation, upper pivot pin 31 remains engaged with distal end 56 of upper slot 32.

Figure 4:
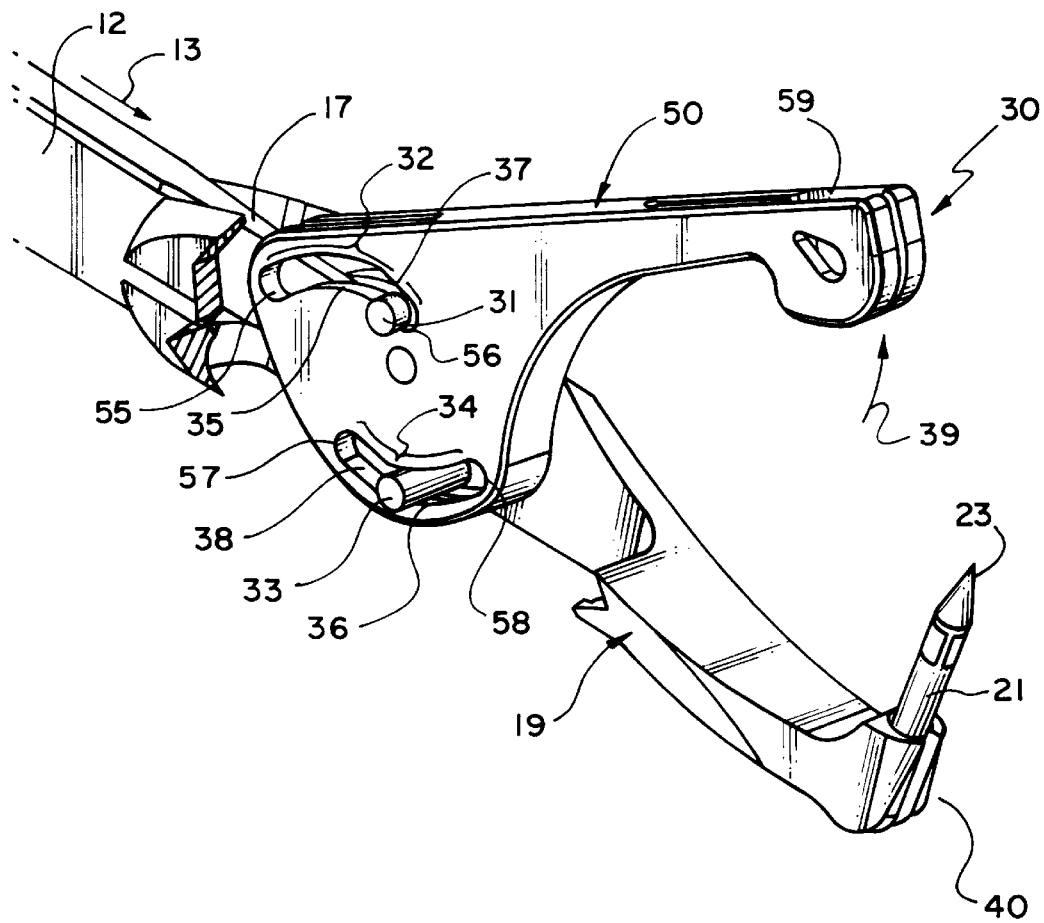
FIG. 4 is an enlarged, partially cut-away view of the suturing assembly of FIG. 2 in transition from the delivery position to an open, misaligned position.

Referring to FIG. 4, upper jaw 50 is now fully open, but is still misaligned relative to mount 40. Continued squeezing of finger section 16 causes pivot pin 33 to slide proximally along linear section 38 so that upper jaw 50 linearly shifts or translates axially until the upper jaw is in the open, aligned position with needle receiving passage 51. Needle receiving passage 51 is now in position to capture needle 21 were the upper jaw to be closed. In this open, aligned position, pivot pins 31, 33 are in contact with ends 56, 57 of slots 32, 34, respectively, (see FIG. 3.)

Figure 5:
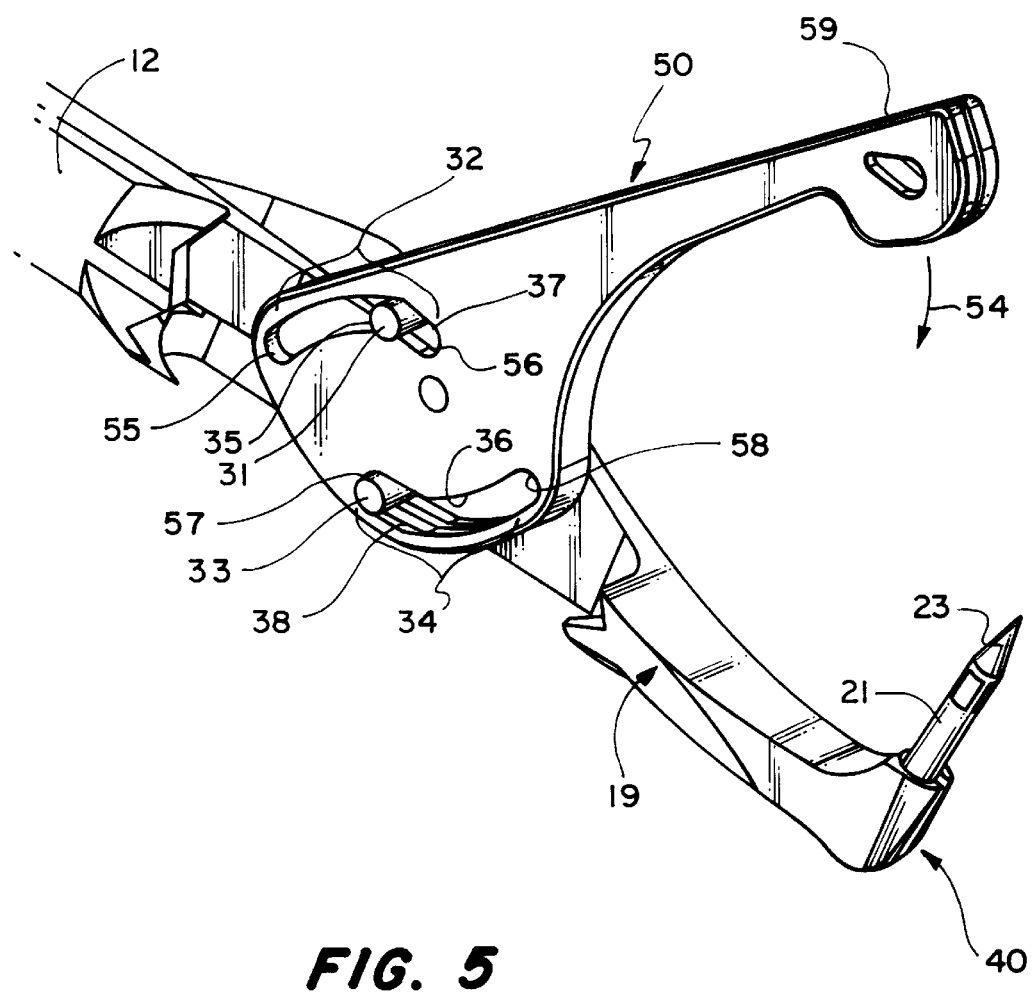
FIG. 5 is a partially cut-away perspective view of the suturing assembly of FIG. 2 in transition from an open, aligned position to a closed position.

Referring to FIG. 5, with pivot pin 33 engaged with proximal end 57 of lower slot 34, further squeezing of finger section 16 causes upper jaw 50 to pivot about pivot pin 33 along arcuate path 65 of upper slot 32. Upper jaw 50, in turn, pivots toward mount 40 in the direction of arrow 54. Throughout this rotation, lower pivot pin 33 remains engaged with proximal end 57 of lower slot 34.

Figure 6:
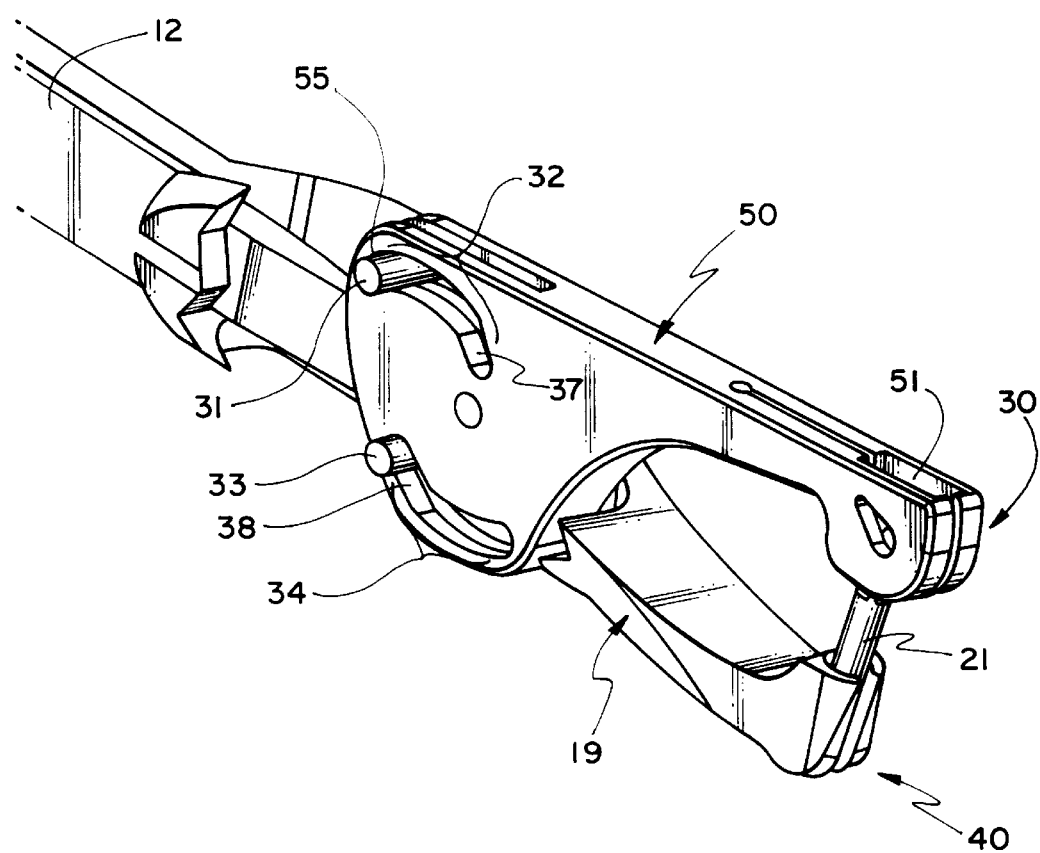
FIG. 6 is a partially cut-away perspective view of the suturing assembly of FIG. 2 with the needled suture engaged in the upper jaw of the assembly in the closed position.

Referring to FIG. 6, when pivot pin 31 contacts proximal end 55 of upper slot 32, upper jaw 50 is in its closed position and needle 21 is captured within needle receiving passage 51 of the upper jaw.

To reverse the process, finger section 16 is pushed away from thumb section 15 so that actuator 17 moves proximally, causing upper jaw 50 with captured needle 21 to pivot away from mount 40 to the open, aligned position. Continued spreading of finger section 16 from thumb section 15 causes upper jaw to linearly retract into the open, misaligned positioned and then to pivot back toward mount 40 to the low profile delivery position. Needled suture 20 is then removed from upper jaw 50, placed again into lower jaw 40, and, if necessary, the procedure is repeated.

Because suturing assembly 30 has a low profile in the delivery position, it can be delivered to the surgical site through a relatively small cannula (e.g., 8 mm inner diameter) extending to a surgical site. Using a smaller cannula allows smaller incisions or portals to be made in the body. Suturing assembly 30 would not be able to fit through the smaller cannula with upper jaw 50 in its open suturing position. Specific details of using a forceps with a cannula and arthroscope are described in co-pending application U.S. Ser. No. 08/603,859 entitled "Suture Passing Forceps" assigned to the assignee of the present invention and incorporated herein by reference.

Other embodiments are within the scope of the claims.

For example, the slot and pin arrangement of pivot mechanism 60 shown in FIGS. 1 through 6 may be configured differently without compromising the performance of suture-passing forceps 10. For example, in the embodiment described above the pivot slots were formed within the upper jaw and the pivot pins were provided as part of the mount. In other embodiments, the position of the pivot pins and slots relative to the upper jaw and mount can be reversed. Alternatively, the upper jaw and mount can each include one pivot slot and one pivot pin.

The slot and pin arrangement of pivot mechanism 60 may be further adjusted to change the degree to which the upper jaw opens relative to the mount, as well as to change the amount of linear translation. For example, by changing the length of the linear sections of the slots, the axial spacing of the upper jaw relative to the mount can be changed.

Figure 7:
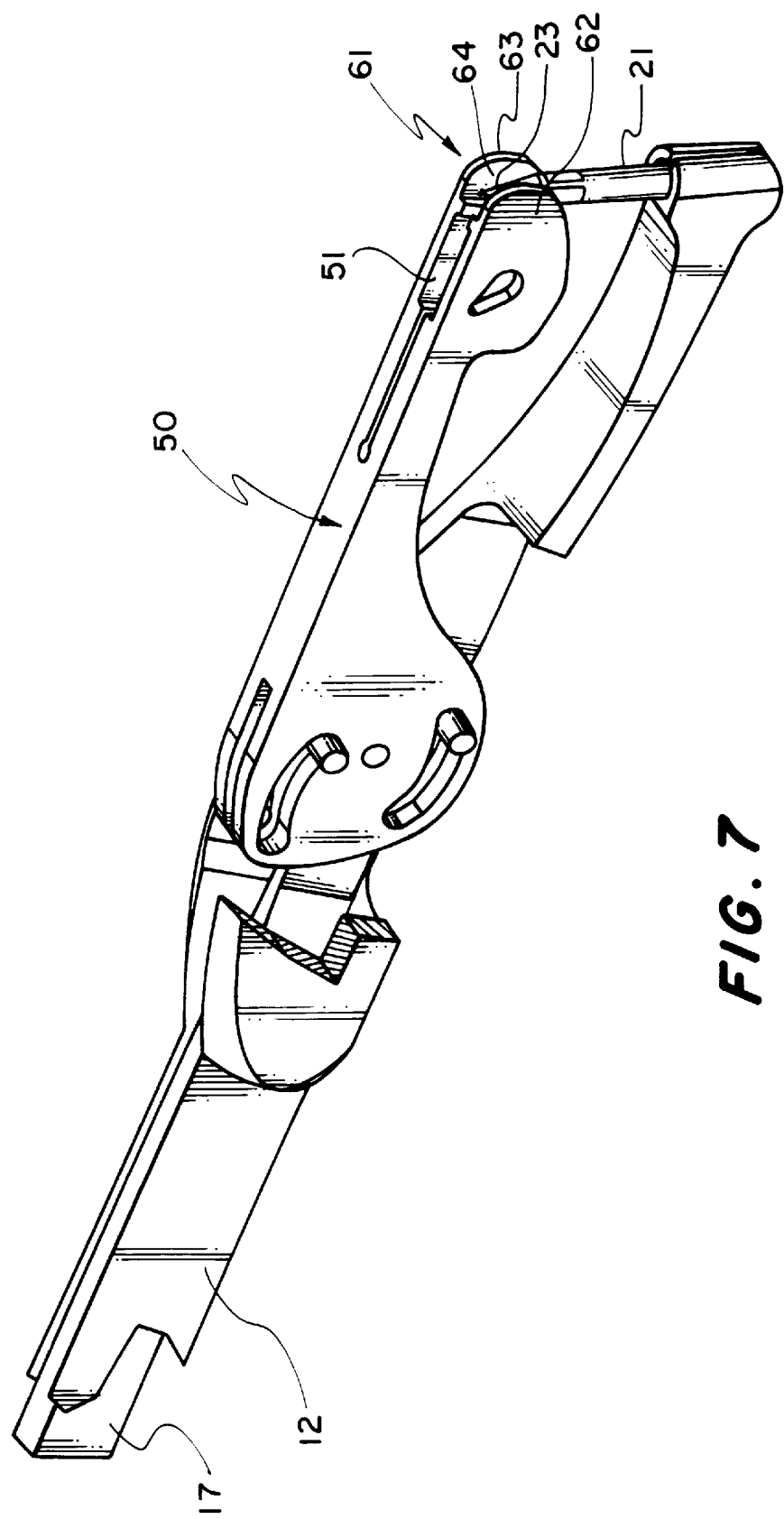
FIG. 7 is a partially cut-away perspective view of an alternative embodiment of the suturing assembly of FIG. 2 having a needle tip protector.

Referring to FIG. 7, in another embodiment, upper jaw 50 may be arranged to include a needle tip protector 61 to protect needle tip 23 when needle 21 is in its delivery position. Needle tip protector 61 includes sidewalls 62, 63 which define needle receiving passage 51 of upper jaw 50 and extend distally to form a slightly-open slot 64 in upper jaw 50. Slot 64 retains pointed tip 23 of needle 21 in the delivery position. This arrangement minimizes tissue snagging by needle 21 during delivery and prior to suturing.

Alternatively, needle receiving passage 51 of upper jaw 50 can be axially misaligned distally relative to mount 40 when in the delivery position. In this embodiment, a region of upper jaw 50 proximal to needle receiving passage 51 can serve as a needle tip protector. In this embodiment, upper and lower pivot pins 31, 33 would be arranged to contact distal ends 55, 57 of upper and lower pivot slots 32, 34 with mount 40 and jaw 50 in the delivery position. In transition from the delivery position to the open, misaligned position, upper jaw 50 pivots in a counter-clockwise direction about lower pivot pin 33. In transition from the open, aligned position to the closed position, upper jaw 50 pivots about upper pivot pin 31 in a clockwise direction. As discussed above, the slot and pin arrangement of pivot mechanism 60 may further be adjusted according to the size of cannula used in delivering suture-passing forceps 10.

In other embodiments, needle 21 can have a curved shape. In this case, passage 42 of mount 40 has a shape formed to accommodate the curved shape of the needle.

Other features and advantages will become apparent from the following description, and from the claims.

What is claimed is:

1. A surgical instrument for manipulating a needle with attached suture, comprising:

an elongated shaft including a distal region having a first jaw with a mount for supporting the needle; and a second jaw mounted to the distal region and having a passage which, when aligned with the mount, is positioned to receive the needle from the mount, the second jaw being pivotable, with respect to the first jaw, between a delivery position in which the second jaw is spaced relatively closely to the mount with the passage misaligned with the mount and an open, misaligned position, the second jaw being axially translatable relative to the mount to an open, aligned position in which the passage is aligned with the mount.

2. The surgical instrument of claim 1, wherein the second jaw is pivotable with respect to the mount between the delivery position and the open, misaligned position along a first arcuate path, said second jaw being axially translatable with respect to the mount to the open, aligned position along a linear path.

3. The surgical instrument of claim 2, wherein the second jaw is pivotable between the open, aligned position to a closed position along a second arcuate path in which the passage is aligned with the mount and in position to receive the needle from the mount.

4. The surgical instrument of claim 3, wherein the second jaw includes a first pivot slot and the first jaw includes a first pivot pin movably retained within the first pivot slot, the first pivot pin defining a center of rotation for the first arcuate path.

5. The surgical instrument of claim 4, wherein the second jaw includes a second pivot slot and the first jaw includes a second pivot pin movably retained within the second pivot slot, the second pivot pin defining a center of rotation for the second arcuate path.

6. The surgical instrument of claim 5, wherein the first and second pivot slots each include arcuately-shaped sections extending to linear sections, the first pivot pin positioned within the linear section of the first pivot slot and the second pivot pin positioned within the arcuately-shaped section of the second pivot slot when the second jaw is pivotable along the first arcuate path.

7. The surgical instrument of claim 6, wherein the second pivot pin is positioned within the linear section of the second pivot slot and the first pivot pin is positioned within the arcuately-shaped section of the first pivot slot when the second jaw is pivotable along the second arcuate path.

8. The surgical instrument of claim 7, wherein the first and second pivot pins are positioned within the linear sections of the first and second pivot slots, respectively as the second jaw is translatable along the linear path.

9. The surgical instrument of claim 6, wherein the linear section of the first pivot slot is substantially parallel to the linear section of the second pivot slot.

10. The surgical instrument of claim 9, wherein the linear sections of the first and second pivot slots are substantially parallel to a longitudinal axis of the elongated shaft when the second jaw is translatable along the linear path.

11. The surgical instrument of claim 1 wherein the passage of the second jaw is positioned proximally of the mount of the first jaw in the delivery position.

12. The surgical instrument of claim 3, further comprising an actuator having a distal end coupled to the second jaw; and a handle disposed at a proximal end of the shaft and coupled to a proximal end of the actuator, the handle being actuatable from a fully open position to a fully closed position to axially move the actuator to move the second jaw from the delivery position, through the open position, and to the closed position.

13. The surgical instrument of claim 1, further comprising a needle tip protector axially offset from the passage of the second jaw.

14. The surgical instrument of claim 13, wherein the needle tip protector is offset proximally from the passage of the second jaw.

15. The surgical instrument of claim 13, wherein the needle tip protector is offset distally from the passage of the second jaw.

16. The surgical instrument of claim 1, wherein the first jaw is stationary relative to the elongated shaft.

17. A method of delivering a needle with attached suture to a surgical site, the method comprising:

provjding a surgical instrument including an elongated shaft with a distal region having a first jaw with a mount for the needle, and a second jaw mounted to the distal region and having a passage for receiving the needle from the mount;

positioning the needle in the mount;

moving the second jaw relative to the first jaw to position the surgical instrument in a delivery position with the second jaw spaced relatively close to the mount and the passage of the second jaw misaligned with the mount;

delivering the surgical instrument to a surgical site; and pivoting the second jaw relative to the mount from the delivery position into an open, misaligned position in which the second jaw is spaced further away from the mount; and translating the second jaw relative to the mount to an open, aligned position in which the passage is aligned with the mount.

18. The method of claim 17, wherein pivoting the second jaw is along a first arcuate path and translating the second jaw is along a linear path.

19. The method of claim 17, further comprising after translating the second jaw into the open, aligned position, actuating the second jaw to pivot the surgical instrument to a closed position by punching the needle through tissue to be sutured and capturing the needle by the passage of the second jaw.

20. The method of claim 19, further comprising after actuating the surgical instrument from the open suturing position to the closed position, withdrawing the surgical instrument from the surgical site, removing the needle from the passage of the second jaw, and repositioning the needle in the mount of the first jaw.

21. The method of claim 17, wherein delivering the surgical instrument includes passing the surgical instrument in the delivery position through a cannula which extends from a portal to the surgical site.

22. The method of claim 17 wherein positioning the needle further includes protecting a pointed tip of the needle in the delivery position by positioning the pointed tip within a needle tip protector formed at a distal end of the second jaw.

* * * * *

US006051006C1

(12) EX PARTE REEXAMINATION CERTIFICATE (6028th)
United States Patent
Shluzas et al.

(10) Number: US 6,051,006 C1
(45) Certificate Issued: Dec. 4, 2007

(54) SUTURE-PASSING FORCEPS

(75) Inventors: Alan E. Shluzas, Millis, MA (US); George Sikora, Mansfield, MA (US)

(73) Assignee: Smith & Nephew, Inc., Memphis, TN (US)

Reexamination Request:
No. 90/006,253, Mar. 22, 2002

Reexamination Certificate for:
Patent No.: 6,051,006
Issued: Apr. 18, 2000
Appl. No.: 09/290,203
Filed: Apr. 12, 1999

(51) Int. Cl.
*A61B 17/04* (2006.01)
*A61B 17/28* (2006.01)

(52) U.S. Cl. .................................. 606/148; 606/144
(58) Field of Classification Search ............... 606/144, 606/148
See application file for complete search history.

(56) References Cited

U.S. PATENT DOCUMENTS

| 4,890,615 | A | | 1/1990 | Caspari et al. | |
|---|---|---|---|---|---|
| 4,923,461 | A | | 5/1990 | Caspari et al. | |
| 4,957,498 | A | | 9/1990 | Caspari et al. | |
| 5,222,962 | A | | 6/1993 | Burkhart | |
| 5,397,325 | A | | 3/1995 | Della Badia et al. | |
| 5,454,823 | A | | 10/1995 | Richardson et al. | |
| 5,522,820 | A | | 6/1996 | Caspari et al. | |
| 5,690,652 | A | * | 11/1997 | Wurster et al. | 606/144 |
| 5,690,653 | A | | 11/1997 | Richardson et al. | |
| 5,843,099 | A | | 12/1998 | Nichols et al. | |
| 5,879,371 | A | | 3/1999 | Gardiner et al. | |
| 5,980,538 | A | * | 11/1999 | Fuchs et al. | 606/145 |
| 6,074,401 | A | * | 6/2000 | Gardiner et al. | 606/139 |
| 6,149,658 | A | * | 11/2000 | Gardiner et al. | 606/139 |
| 6,511,487 | B1 | | 1/2003 | Oren et al. | |
| 6,551,330 | B1 | | 4/2003 | Bain et al. | |
| 6,638,283 | B2 | | 10/2003 | Thal | |
| 2002/0065526 | A1 | | 5/2002 | Oren et al. | |
| 2002/0103493 | A1 | | 8/2002 | Thal | |
| 2002/0138084 | A1 | | 9/2002 | Weber | |
| 2003/0233106 | A1 | | 12/2003 | Dreyfuss | |

FOREIGN PATENT DOCUMENTS

| EP | 0 315 371 | 10/1988 |
|---|---|---|
| EP | 0 535 906 | 3/2000 |
| EP | 1 243 221 | 9/2002 |
| EP | 0 903 109 | 7/2003 |
| WO | WO 98/30151 A | 7/1998 |
| WO | WO 98/30152 A | 7/1998 |
| WO | WO 98/30153 A | 7/1998 |
| WO | WO 98/43545 A | 10/1998 |
| WO | WO02/43558 | 6/2002 |

* cited by examiner

*Primary Examiner*—Gary Jackson

(57) ABSTRACT

A surgical instrument (e.g., suture-passing forceps) has a first jaw with a mount which supports a needled suture and a second jaw having a passage, which when aligned with the mount, is positioned to receive the needled suture. The second jaw is positioned relative to the mount in a manner which allows delivery of the instrument to a surgical site in a low profile, delivery position (e.g., with the jaws spaced relatively closely). The surgical instrument includes an elongated shaft having a distal region for supporting the jaws. The second jaw is pivotable, with respect to the mount, between the delivery position in which the second jaw is spaced relatively closely to the mount with the passage misaligned with the mount and an open, misaligned position, the second jaw being axially translatable relative to the mount to an open, aligned position in which the passage is aligned with the mount.

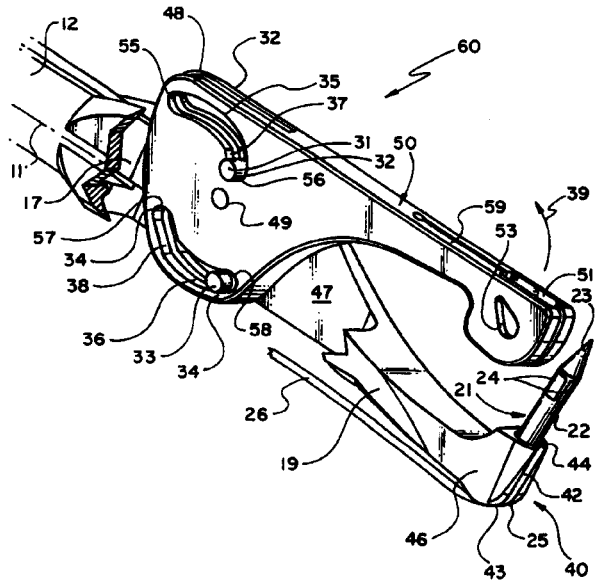

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 17 are determined to be patentable as amended.

Claims 2–16 and 18–22, dependent on an amended claim, are determined to be patentable.

New claims 23–28 are added and determined to be patentable.

1. A surgical instrument for manipulating a needle with attached suture, comprising:
   an elongated shaft including a distal [region] *end* having a first jaw with a mount for supporting the needle; and
   a second jaw [mounted to the distal region] *moveably secured to the distal end of the shaft* and having a passage which, [when aligned with the mount,] is [positioned] *dimensioned* to receive the needle from the mount, the second jaw being [pivotable,] *moveable* with respect to the first jaw *by axial translation and rotatable about a point which is stationary with respect to both the first jaw and the second jaw during rotation*, between a delivery position in which the second jaw is spaced relatively closely to the mount with the passage misaligned with the mount and an open[, misaligned position, the second jaw being axially translatable relative to the mount to an open,] aligned position in which the passage is aligned with the mount.

17. A method of delivering a needle with attached suture to a surgical site, the method comprising:
    providing a surgical instrument including an elongated shaft with a distal [region] *end* having a first jaw with a mount for the needle, and a second jaw [mounted to the distal region] *moveably secured to the distal end of the shaft* and having a passage for receiving the needle from the mount;
    positioning the needle in the mount;
    moving the second jaw relative to the first jaw to position the surgical instrument in a delivery position with the second jaw spaced relatively close to the mount and the passage of the second jaw misaligned with the mount;
    delivering the surgical instrument to a surgical site; [and]
    pivoting the second jaw [relative to the mount] *about an axis of rotation which is stationary with respect to both the first jaw and the second jaw* from the delivery position into an open, misaligned position in which the second jaw is spaced further away from the mount; *and*
    *translating the second jaw relative to the mount to an open, aligned position in which the passage is aligned with the mount.*

*23. The surgical instrument of claim 1 wherein the second jaw is pivotable at the distal end of the elongated shaft.*

*24. The surgical instrument of claim 5 wherein the center of rotation for the first arcuate path and the center of rotation for the second arcuate path are at the distal end of the elongated shaft.*

*25. The method of claim 17, wherein the second jaw includes a first pivot slot and the first jaw includes a first pivot pin movably retained within the first pivot slot, the first pivot pin defining a center of rotation for the first arcuate path.*

*26. The method of claim 25, wherein the second jaw includes a second pivot slot and the first jaw includes a second pivot pin movably retained within the second pivot slot, the second pivot pin defining a center of rotation for the second arcuate path.*

*27. The method of claim 17 wherein the second jaw is pivotable at the distal end of the elongated shaft.*

*28. The method of claim 25 wherein the center of rotation for the first arcuate path and the center of rotation for the second arcuate path are at the distal end of the elongated shaft.*

\* \* \* \* \*